United States Patent [19]

Lepp et al.

[11] 4,260,678

[45] Apr. 7, 1981

[54] DETERMINING CREATINE KINASE ISOENZMES VIA IMMOBILIZED ANTIBODY-ISOENZYME COMPLEXES

[75] Inventors: Cyrus A. Lepp, Corning; Gerald Odstrchel, Horseheads, both of N.Y.

[73] Assignee: Corning Glass Works, Corning, N.Y.

[21] Appl. No.: 14,315

[22] Filed: Feb. 23, 1979

[51] Int. Cl.³ .................... C12Q 1/65; C12Q 1/50
[52] U.S. Cl. .......................... 435/7; 435/17; 424/2; 23/230 B
[58] Field of Search ............... 435/7, 17; 23/230 B; 424/2, 12

[56] References Cited

U.S. PATENT DOCUMENTS

| | | |
|---|---|---|
| 3,652,761 | 3/1972 | Weetall ............................... 435/7 |
| 3,839,153 | 10/1974 | Schuurs et al. ....................... 435/7 |
| 3,994,783 | 11/1976 | Rao et al. ............................ 435/17 |
| 4,012,285 | 3/1977 | Pfleider et al. ...................... 424/12 |
| 4,067,775 | 1/1978 | Wurzburg et al. ..................... 435/7 |

FOREIGN PATENT DOCUMENTS

1535669 12/1978 United Kingdom.

OTHER PUBLICATIONS

Smith, "Separation of Tissue and Serum Creatine Kinase Isoenzymes on Polyacrylamide Gel Slabs", *Clin. Chem. Acta*, vol. 39 (1972) pp. 351–359.
Somer, et al., "A Method Allowing the Quantitation of Serum Creatine Kinase Isoenzymes", *Clin. Chem. Acta*, vol. 36 (1972) pp. 531–536.
Wagner, et al. "The Importance of Identification of the Myocardial-Specific Isoenzyme of Creatine Phosphokinase of (MB form) in the Diagnosis of Acute Myocardial Infarction", *Circulaton*, vol. 47 (1973) pp. 263–269.
Mercer, "Separation of Tissue and and Serum Creatine Kinase Isoenzymes by Ion-Exchange Column Chromatography", *Clin. Chem.*, vol. 20, No. 1 (1974) pp. 36–40.
Jockers-Wretou, et al., "Qantitation of Creatine Kinase Isoenzymes in Human Tissues and Sera by an Immunological Method", *Clin. Chem Acta*, vol. 58 (1975) pp. 223–232.
Neumeir, et al., =Immunological Nachweiss von Creatine-MBin Serum beim Myo Kardin farkt", *Klin. Wochenschv.*, vol. 53, (1975) pp. 329–333.
Neumeier, et al, "Radioimmunoassay For Sublimit B in Isoenzymes CK-MB and CK-BB of Creatine Phospho Kinase", *Clin. Chem. Acta*, vol. 79 (1977) pp. 107–113.
Roberts, et al., "Immunological Detection of Myocardial Infarction with a Radioimmunoassay for MB Creatine Kinase", *Clin. Chem. Acta*, vol. 83 (1978) pp. 141–149.
Van Steirteghem, et al., "Radioimmunoassay of Creatine Kinase Iosenzymes in Human Serum: Isoenzyme MM", *Clin. Chem.* vol. 24, No. 3, (1978) pp. 414–422.
Zweig, et al. "Radioimmunoassay of Creatine Kinase Isoenzymes in Human Serum Isoenzyme BB", *Clin. Chem.*, vol. 24, No. 3 (1978), pp. 422–428.
Perriard, et al., "Quantitation of Creatine Kinase Isoenzyme Transition in Differentiating Chicken Embryonic Breast Muscle and Myogenic Cell Cultures by Immunoadsorption", *Arch Biochem Bisphys* vol. 191, No. 1 (1978) pp. 90–100.
Williams, et al., *Methods in Immunology and Immunochemistry*, vol. IV, (1977) Acadamic Press, NY, pp. 316–317.
Lepp, et al. "A New Method for the Isolation and Purification of Creatine Kinase", *J. Solid-Phase Biochem.*, vol. 2, No. 2 (1977) pp. 183–185.
Neumeier et al., "Determination of Creatine Kinase Isoenzyme MB Activity in Serum Using Immunological Inhibition of Creatine Kinase M Subunit Activity", *Clin. Chem. Acta*, vol. 73 (1976) pp. 445–451.

*Primary Examiner*—Thomas G. Wiseman
*Attorney, Agent, or Firm*—William E. Maycock

[57] ABSTRACT

Creatine kinase isoenzymes in a liquid sample are determined by means of immobilized antibody-isoenzyme complexes in which measureable isoenzyme activity is retained.

15 Claims, No Drawings

4,260,678

DETERMINING CREATINE KINASE ISOENZYMES VIA IMMOBILIZED ANTIBODY-ISOENZYME COMPLEXES

BACKGROUND OF THE INVENTION

This disclosure relates generally to methods for determining the presence of creatine kinase isoenzymes in a sample. More specifically, this disclosure relates to a method for determining, either qualitatively or quantitatively, the presence of creatine kinase isoenzymes in a sample via immobilized antibody-isoenzyme complexes.

It was demonstrated in 1964 that human tissues contain three principal isoenzymes of creatine kinase (CK, E.C. 2.7.3.2, also known as creatine-ATP-transphosphorylase) which are composed of two unique subunits, M and B, in different combinations. See, e.g., A. Burger et al., *Biochem. Z*, 339, 305 (1964); D. H. Deul and J. F. L. van Bremen, *Clin. Chim. Acta*, 10, 276 (1964); and K. Sjovall and A. Voight, *Nature*, 202, 701 (1964). Thus, such isoenzymes consist of an anodal isoenzyme (BB) present in brain, an isoenzyme (MM) with electrophoretic mobility corresponding to $\gamma$-globulin present in skeletal muscle, and an isoenzyme (MB) of intermediate electrophoretic mobility present in some skeletal muscles and in myocardium.

During the next ten years, researchers studied the separation and quantitation of CK isoenzymes, primarily by electrophoretic techniques, and proposed that the MB isoenzyme provides a sensitive and specific indication of acute myocardial infarction. See, for example, A. F. Smith, *Clin. Chim. Acta*, 39, 351 (1972); H. Somer and A. Konttinen, *Clin. Chim. Acta*, 36, 531 (1972); and G. S. Wagner et al., *Circulation* 47, 263 (1973). The separation of CK isoenzymes also was achieved by ion-exchange column chromatography. D. W. Mercer, *Clin. Chem.*, 20, 36 (1974).

More recently, other, perhaps less traditional, methods have been applied to the separation and/or quantitation of the CK isoenzymes. One such method is immunotitration or immunoinhibition. According to E. Jockers-Wretou and G. Pfleiderer, *Clin. Chim. Acta*, 58, 223 (1975), antisera against the crystallized CK isoenzymes from human skeletal muscle (MM) and from human brain (BB) were produced in rabbits. Both the MM and BB isoenzymes were quantitatively precipitated by their homologous antisera, with no cross-reaction being observed. The hybrid MB isoenzyme from human heart muscle could not be precipitated completely by either of the two antisera. The concentrations of the three creatine kinase isoenzymes in artificial mixtures were then determined from the percentage of non-precipitable activity in the supernatant after reaction with each of the antisera. Because about ten percent residual activity always remained in the supernatant, even with a large excess of antiserum present, it was assumed that such activity resulted from the presence of MB. Consequently, the calculations leading to a value for MB activity were based upon such assumption.

An immunological method very similar to the above is that of D. Neumeier et al., *Klin. Wochenschr.*, 53, 329 (1975); see also U.S. Pat. No. 4,067,775 to U. Wurzburg et al. These workers report that MM and MB are quantitatively precipitated by the MM antiserum. Similarly, BB and MB are quantitatively precipitated by the BB antiserum. Furthermore, BB reportedly is not present in the serum. Consequently, the method involves first determining total CK activity. Activity remaining in the supernatant after precipitation with BB antiserum then is measured. The difference between the two values allegedly represents MB activity in the serum sample.

Radioimmunoassays for the CK isoenzymes also are known. According to D. Neumeier et al., *Clin. Chim. Acta*, 79, 107 (1977), the subunit B in MB and BB is quantitated by means of a double-antibody radioimmunoassay which utilizes $^{125}$I-labeled BB antiserum. A competitive displacement radioimmunoassay for MB, utilizing $^{125}$I-labeled CK isoenzymes, was reported by R. Roberts et al., *Clin. Chim. Acta*, 83, 141 (1978). Finally, double-antibody radioimmunoassays for MM and BB using $^{125}$I-labeled isoenzymes were reported by A. C. Van Steirteghem et al., *Clin. Chem.*, 24, 414 (1978) and M. H. Zweig et al., *Clin. Chem.*, 24, 422 (1978), respectively.

Finally, an immunoadsorbent procedure for quantitating CK isoenzymes was reported by J. Perriard et al., *Arch. Biochem. Biophys.*, 191 90, (1978). The procedure involved preparing pure MM and BB antisera and separately coupling such antisera to cyanogen bromide-activated Sepharose 4B. The total CK activity in a sample then was determined. Aliquots of the sample were passed over each immunoadsorbent column and unbound isoenzyme was washed off each column. Unbound isoenzyme activity then was measured in each case. Thus, unbound activity from the anti-MM column represented BB activity and MM activity was the unbound activity from the anti-BB column. MB activity then was determined by subtracting the MM and BB activities from the total CK activity in the sample.

In all of these prior art methods, isoenzyme activity of the isoenzyme-antibody complexes was either presumed or known to be nonexistent. This, of course, is consistent with the known CK isoenzyme antibody inactivation. See, for example, C. A. Williams and M. W. Chase, Editors, "Methods in Immunology and Immunochemistry", Volume IV, Academic Press, New York, 1977, p. 317; B. Cinader, Editor, "Antibodies to Biologically Active Molecules", Volume 1, Proceedings of the 2nd Meeting of the Federation of European Biochemical Societies, Vienna, 21-24 April 1965, Pergamon Press, Symposium Publications Division, Oxford, 1967, p. 87; B. Cinader, *Ann. N. Y. Acad. Sci.*, 103(2), 500 (1963); and M. R. J. Salton, Editor, "Immunochemistry of Enzymes and Their Antibodies", John Wiley & Sons, New York, 1977, p. 104.

Thus, no reports are known in which the presence of CK isoemzymes was demonstrated by measuring the CK isoenzyme activity of an antibody-isoenzyme complex.

SUMMARY OF THE INVENTION

It therefore is an object of the present invention to provide a method for determining the presence of CK isoenzymes.

Another object of the present invention is to provide a method for determining the presence of CK isoenzymes by means of immobilized antibody-isoenzyme complexes.

A further object is to provide a method for determining the presence of CK isoenzymes by means of immobilized antibody-isoenzyme complexes in which measurable isoenzyme activity is retained.

These and other objects will be apparent to those skilled in the art from a consideration of the specification and claims which follow.

It has been discovered, quite unexpectedly, that immobilized antibody specific for a given CK isoenzyme will bind with the isoenzyme to form an immobilized antibody-isoenzyme complex with a measurable retention of the isoenzyme activity, i.e., without complete inhibition of isoenzymatic activity.

Accordingly, the present invention provides a method for determining the presence of CK isoenzymes in a fluid sample which comprises bringing immobilized antibody specific for a given CK isoenzyme into contact with such sample, isolating the immobilized antibody or resulting immobilized antibody-isoenzyme complex or mixture thereof, and then testing the isolated material for isoenzymatic activity.

The present invention also provides a method for determining the presence of CK isoenzymes in a fluid sample which comprises the steps of:

A. combining the fluid sample or an aliquot thereof with an immobilized antibody specific for a given CK isoenzyme;

B. incubating the mixture resulting from step A;

C. separating from the incubated mixture of step B the immobilized antibody or resulting immobilized antibody-isoenzyme complex or mixture thereof; and D. assaying the material obtained from step C for isoenzyme activity.

The determination of the presence and quantity of various of the CK isoenzymes in human serum can be useful in diagnosing a number of disorders, such as myocardial infarction, traumata of the heart, advanced progressive muscular dystrophy, dermatomyositis, diseases which entail a myoglobinuria, and malignant hyperthermia.

DETAILED DESCRIPTION OF THE INVENTION

As used herein, the term "fluid sample" refers either to original, fluid samples or to samples converted to a fluid form subsequent to sample collection. Thus, the fluid sample can be either an extract of human tissue or human serum, pleural fluid, urine, spinal fluid, or semen. As a practical matter, the fluid sample most often will consist of human serum.

In some cases, it may be either desirable or necessary to determine the total CK isoenzyme activity in the fluid sample. As discussed hereinafter, the present invention provides a method for such a determination. Alternatively, any of the well-known, prior-art procedures can be employed. It will be apparent that the determination of total CK isoenzyme activity can be carried out before, during, or after the method of the present invention.

Thus, the first step of the method of the present invention comprises combining the fluid sample or an aliquot thereof with an immobilized antibody specific to a given CK isoenzyme. In general, antibody specific for the isoenzyme is generated in accordance with known procedures. Typically, however, the antiserum thus obtained is not further processed to give purified antibody. As a matter of convenience, the immobilized antibody is prepared directly from the antiserum. Thus, the immobilized antibody inevitably has associated with it immobilized proteins, e.g., globulins, of various types, none of which are significant in terms of the method of the present invention. Thus, the term "immobilized antibody" does not require any particular degree of purity, although it will be apparent to those skilled in the art that immobilized antibody preparations derived directly from antiserum will require more of such preparation per unit of enzyme activity than such a preparation derived from purified antiserum.

The immobilization of antibody in turn is carried out in accordance with well-known procedures. In general, neither the carrier nor the immobilization procedure is critical, provided that significant deleterious effects are avoided. Thus, the carriers can be organic or inorganic, porous or nonporous, and in any desired shape or form. The carrier can be particulate in nature, varying from a finely-divided powder to a coarse granular material, or the carrier can be a continuous, shaped article such as a flat or curved sheet or pellet, or a three-dimensional article such as a rectangular or cylindrical tube or a complex monolith. As a practical matter, the carrier most often will be particulate and relatively finely divided, e.g., from about 20 to about 100 mesh, U.S. Standard Sieve.

Examples of suitable organic carriers include, among others, polyesters, such as poly(ethylene terephthalate); polyamides, such as nylon 6 and nylon 6.6; polyacrylates; polymethacrylates; agarose gels; dextran gels; polyolefins, such as polyethylene, polypropylene, polybutene, and polybutadiene; polystyrene; poly(vinyl chloride); poly(vinylidene chloride); and the like.

The inorganic carriers can be classified as siliceous or nonsiliceous metal oxides. Examples of siliceous carriers include glass, silica, wollastonite, bentonite, cordierite, and the like. Examples of nonsiliceous metal oxides include, among others, alumina, spinel, apatite, nickel oxide, titania, zirconia, and the like. The preferred carriers are inorganic in nature, with siliceous materials being more preferred. The most preferred carriers are silica and glass. Preferably, the carrier will be porous in order to provide a greater amount of antibody per unit volume or mass of carrier.

In general, the antibody can be immobilized by any known means which can vary from simple adsorption to chemical coupling. Adsorption, of course, usually involves contacting an aqueous solution of the antibody (antiserum) to be immobilized with the carrier for a time sufficient to permit the desired (or maximum) degree of immobilization. Chemical coupling typically involves treating the carrier with one or more chemical compounds, followed by contacting the treated carrier with an aqueous solution of the antibody. Among the chemical compounds which can be used to treat the carrier, and especially the inorganic carrier, are o-dianisidine (U.S. Pat. No. 3,983,000), polymeric isocyanates (U.S. Pat. No. 4,071,409), silanes (U.S. Pat. Nos. 3,519,538 and 3,652,761), and the like. See also U.S. Pat. Nos. 3,930,951 and 3,933,589.

The second step of the present invention comprises incubating the mixture resulting from the first step. Such incubation typically is carried out at a temperature of from about 4° C. to about 40° C. An especially suitable temperature is 37° C. Incubation times are not critical, and generally will vary from about 0.5 to about 3 hours. As a practical matter, however, incubation times in excess of one hour seldom are required.

According to the third step of the method of the present invention, the immobilized antibody or resulting immobilized antibody-isoenzyme complex or mixture thereof is separated from the incubated mixture of the second step. Such separation can be by any known means, such as centrifugation and filtration, although centrifugation is particularly effective and is preferred.

The fourth step comprises assaying the material obtained from the third step for isoenzyme activity. Such assay can be accomplished by any known means and can be either qualitative or quantitative.

It is, of course, well known that the CK isoenzymes catalyze the following reaction:

wherein ADP and ATP represent adenosine 5'-diphosphate and adenosine 5'-triphosphate, respectively. Additionally, the following reactions also are well known:

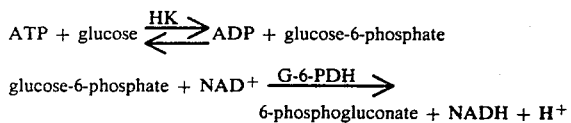

wherein HK represents hexokinase; NAD+ represents the oxidized form, and NADH the reduced form, of nicotinamideadenine-dinucleotide; and G-6-PDH represents glucose-6-phosphate dehydrogenase. Consequently, a particularly useful substrate for determining the presence of CK isoenzymes, and one which is commercially available, contains creatine phosphate, ADP, glucose, NAD+, hexokinase, and glucose-6-phosphate dehydrogenase. Such a substrate permits the ready detection or measurement of NADH, either spectrophotometrically at 340 nm or fluormetrically. An example of such a commercially-available substrate is STATZYME ® CPK n-1 (Worthington Diagnostics, Freehold, New Jersey 07728). Alternatively, the NAD+ and G-6-PDH can be replaced with NADP+ and an enzyme specific therefor, respectively.

Of course, other substrates can be employed, or the detection of substances other than NADH is possible. Additionally, the presence of NADH can be detected by other means. For example, the substrate solution can include a dye which is reducible by NADH, thereby permitting the use of colorimetric procedures using a spectrophotometer. Examples of such dyes include NADH-linked colorimetric dye formulations, such as p-iodonitrotetrazolium violet, nitroblue tetrazolium chloride, or other suitable tetrazolium salt in conjunction with phenazine methosulfate. Alternatively, the G-6-PDH and HK linked reactions can be bypassed by using reagents which couple with a product, such as creatine, of the CK-catalyzed reaction. Thus, α-naphthol and diacetyl can be combined, which combination forms a pink-colored complex in the presence of creatine.

Regardless of the assay procedure employed, the data thus obtained are compared with a standard curve in accordance with well-known procedures, thereby yielding the quantitative determination of the presence of CK isoenzymes.

To determine total CK isoenzyme activity by the method of the present invention, it is only necessary to carry out such method with immobilized antibodies for both MM and BB isoenzymes, using the same fluid sample. Obviously, the procedure can be carried out on a given sample first with immobilized antibody for one of MM and BB, and then with immobilized antibody for the other of MM and BB. More conveniently, however, immobilized antibodies for both MM and BB can be combined, and the resulting mixture utilized in the method of the present invention.

The present invention is further illustrated, but not limited, by the example which follows. Unless otherwise indicated, all temperatures are in degrees celsius.

EXAMPLE

Beef muscle CK isoenzyme MM was isolated and purified in accordance with the procedure of H. J. Keutel et al., Arch. Biochem. Biophys., 150, 648 (1972). Antibody to such isoenzyme then was generated in rabbits in accordance with standard procedures. Immobilized antiserum (immobilized antibody, IMA) was prepared according to Weetall and Filbert, using controlled-pore glass having an average pore diameter of 550 A and an average particle size of one micron, in a ratio of one gram of glass per four ml. of antiserum; see W. B. Jakoby and M. Wilchek, Editors, "Methods in Enzymology", Volume 34B, Academic Press, Inc., New York, 1974, pp. 59–72. Briefly, the glass was cleaned in 5% nitric acid solution, washed, and treated with a 10% solution of γ-aminopropyltriethoxysilane in distilled water at a pH of 3.45. The resulting silanized glass was reacted with p-nitrobenzoyl chloride in chloroform containing ten volume percent triethylamine as a hydrogen chloride scavenger. Reduction of the nitro group then was accomplished by treating the p-nitrobenzoylaminoalkyl derivatized glass with 10% sodium dithionite in water. The resulting p-aminobenzoylaminoalkyl derivatized glass was diazotized with nitrous acid generated in situ from hydrochloric acid and sodium nitrite. The diazotized product was washed and added to antiserum at pH 8–9. The resulting immobilized antibody was isolated by centrifugation, washed, and suspended in pH 7.4 saline buffered with 0.01 M phosphate (pH 7.4 buffered saline) at a level of 10 mg. of IMA per ml. of buffered saline. The IMA thus obtained contained 32 mg. of protein per 100 mg. of glass.

To 0.5 ml of a solution containing a known concentration of the purified beef MM isoenzyme was added 0.5 ml. of the IMA suspension. The resulting mixture was incubated at 37° for 30 minutes. The mixture then was centrifuged to pellet the IMA and IMA-MM complex. The pellet was resuspended in pH 7.4 buffered saline and redeposited by centrifugation to wash the glass free of nonspecifically-bound enzyme or other proteins. The washed pellet then was suspended in 1.0 ml. of STATZYME CPK n-1 and incubated at room temperature (25°); separate samples were incubated for time periods of 2, 5, 10, and 20 minutes. After incubation, the mixture was centrifuged and the optical density of the supernatant at 340 nm was measured on a spectrophotometer. The measurements for each known concentration and time period were averaged to give ΔO.D. per min. for each concentration. Controls (blanks) were run in every case and subtracted from the measured values to give blank-corrected values which are summarized in the following table:

| MM Conc. IU/L | Blank-Corrected ΔO.D./Min. |
|---|---|
| 1000 | 0.099 |
| 500 | 0.076 |

-continued

| MM Conc. IU/L | Blank-Corrected ΔO.D./Min. |
|---|---|
| 250 | 0.048 |
| 125 | 0.028 |
| 62 | 0.016 |
| 32 | 0.011 |
| 16 | 0.002 |
| 8 | 0 |
| 0 | 0 |

The data in the above table were used to construct a standard curve in accordance with well-known procedures.

The above-described procedure was repeated, except that the solutions of MM isoenzyme were replaced with solutions of BB isoenzyme, isolated from beef brain. The following data were obtained:

| BB Conc. IU/l | Blank-Corrected ΔO.D./Min. |
|---|---|
| 660 | 0.008 |
| 165 | 0.006 |
| 0 | 0 |

Thus, with the IMA employed, some cross-reactivity was observed and was estimated to be about 15 percent.

It is to be understood that the foregoing detailed description is given merely by way of illustration and that many variations may be made therein without departing from the spirit of the invention.

What is claimed is:

1. A method for determining the presence of creatine kinase isoenzymes in a fluid sample which comprises bringing immobilized antibody specific for a given creatine kinase isoenzyme selected from MM or BB forms into contact with such sample under conditions suitable for forming an immobilized antibody-isoenzyme complex, isolating the immobilized antibody or resulting immobilized antibody-isoenzyme complex having substantial enzymatic activity or mixture thereof, and then directly testing the isolated immobilized phase for isoenzymatic activity.

2. The method of claim 1 in which the antibody is immobilized on a particulate inorganic support.

3. The method of claim 2 in which the support is siliceous.

4. The method of claim 3 in which the support is controlled-pore glass.

5. The method of claim 1 in which the fluid sample is human serum.

6. A method for determining the presence of creatine kinase isoenzymes in a fluid sample which comprises the steps of:
   A. combining the fluid sample or an aliquot thereof with an immobilized antibody specific for a given creatine kinase isoenzyme selected from BB or MM forms;
   B. incubating the mixture resulting from step A under conditions suitable for forming an immobilized antibody-isoenzyme complex;
   C. separating from the incubated mixture of step B the immobilized antibody or resulting immobilized antibody-isoenzyme complex having substantial isoenzyme activity or mixture thereof; and
   D. directly assaying the immobilized phase obtained from step C for isoenzyme activity.

7. The method of claim 6 in which the antibody is immobilized on a particulate inorganic support.

8. The method of claim 7 in which the support is siliceous.

9. The method of claim 8 in which the support is controlled-pore glass.

10. The method of claim 9 in which the isoenzyme is the BB form.

11. The method of claim 9 in which the isoenzyme is the MM form.

12. The method of claim 6 in which the fluid sample is human serum.

13. The method of claim 12 in which the total creatine kinase isoenzyme activity of the fluid sample also is determined.

14. The method of claim 6 in which the method is carried out with immobilized antibody specific for one of the MM and BB forms of isoenzyme, and then repeated on the same sample using immobilized antibody specific for the other of the MM and BB forms.

15. The method of claim 6 in which the method is carried out using antibody specific for both the MM and BB forms of the isoenzyme.

* * * * *